United States Patent [19]

Dormoy et al.

[11] Patent Number: 4,831,144
[45] Date of Patent: May 16, 1989

[54] 1H-PYRROLO [3,2-C]PYRROLIDINES PROTECTED IN 1-POSITION USEFUL AS INTERMEDIATES

[75] Inventors: Jean-Robert Dormoy; Alain Heymes, both of Sisteron, France

[73] Assignee: SANOFI, Paris, France

[21] Appl. No.: 141,508

[22] Filed: Jan. 7, 1988

Related U.S. Application Data

[63] Continuation-in-part of Ser. No. 806,544, Dec. 9, 1985, abandoned.

[30] Foreign Application Priority Data

Dec. 12, 1984 [FR] France ............................... 84 19029

[51] Int. Cl.$^4$ ........................................... C07D 471/04
[52] U.S. Cl. ...................................... 546/113; 546/14
[58] Field of Search ......................................... 546/113

[56] References Cited

PUBLICATIONS

Ducrocq et al., Tetrahedron 32, pp. 773–780 (1976).
Fisher et al., J. Med. Chem 15(11), pp. 1168–1171 (1972).

*Primary Examiner*—Mary C. Lee
*Assistant Examiner*—Bernard I. Dentz
*Attorney, Agent, or Firm*—Bacon & Thomas

[57] ABSTRACT

The invention relates to a process for fixing an electrophilic group in the 2-position of 1H-pyrrolo[3,2-c]pyridine N-protected in the 1-position, process which consists in protecting the 1-position in question with a labile protecting group, reacting the compound so obtained with a lithiation agent selected from a lithium amide and an alkyl lithium at a temperature between $-80°$ C. and $-20°$ C. and in the presence of tetramethylethylenediamine to obtain the corresponding 2-lithio derivative and then condensing the metal derivative so obtained at a temperature between $-80°$ C. and room-temperature with a reagent capable of giving rise to an electrophilic group to form N-protected 1H-pyrrolo[3,2-c]pyridine substituted in the 2-position by an electrophilic group.

6 Claims, No Drawings

1H-PYRROLO [3,2-C]PYRROLIDINES PROTECTED IN 1-POSITION USEFUL AS INTERMEDIATES

This application is a continuation-in-part of copending application Ser. No. 806,544 filed Dec. 9. 1985 now abandoned.

This invention relates to the preparation of 1H-pyrrolo[3,2-c]pyridine derivatives.

More particularly, the invention concerns a process for fixing an electrophilic group in the 2-position of 1H-pyrrolo[3,2-c]pyridine N-protected in the 1-position.

Only a relatively small number of 1H-pyrrolo[3,2-c]pyridines substituted in the 2-position have been reported so far in the chemical literature. The preparation of such compounds is, in fact, very difficult. For instance, a process of preparing 2-phenyl and 2-(2-fluorophenyl)-1H-pyrrolo[3,2-c]pyridines is cited in J. Med. Chem. 1972, vol. 15, No. 11 pp. 1168–1171 involving a cyclization reaction at high temperature and using strongly basic conditions. These operating conditions can certainly not be used for any substitution in the 2-position of 1H-pyrrolo[3,2-c]pyridine since the authors of that publication reached the conclusion that "the described reaction is unadequate for synthetizing 1H-pyrrolo[3,2-c]pyridine derivatives comprising fragile substituents".

It is thus of prime importance to search for a process which can be easily used for obtaining 1H-pyrrolo[3,2-c]pyridine derivatives substituted in the 2-position whatever the kind of substituents to be fixed may be.

It is, however, not possible to systematically extrapolate to 1H-pyrrolo[3,2-c]pyridine from processes known for the introduction of substituents in the indole ring since a well-known difference exists in the reactivity of these two heterocycles.

It is known, for instance, that reactions on the indole moiety undertaken in an acid medium are difficult to extend to the case of 1H-pyrrolo[3,2-c]pyridine since the pyridine nitrogen is protonated and therefore inactived.

Likewise, J.C.S. Perkin I pp. 138–141 (1979) contains a report of trials carried out for the purpose of preparing pyrido[4,3-b]indole and ethyl-6- or 7-pyrido[4,3-b]indolyl-carboxylates by condensation of 1H-pyrrolo[3,2-c]pyridine with 2,5-hexanedione or ethyl 2,5-dioxo-3-hexylcarboxylate.

Although this type of reaction is known and used in the indole, the above attempts performed from 1H-pyrrolo[3,2-c]pyridine were not successful, probably by reason of the lower degree of reactivity of the pyrrole nucleus in the case of the pyrrolo-pyridine.

Moreover, attempts are reported in Tetrahedron, vol. 39, No. 10 pp. 1777–1781 (1983) to fix a substituent directly in the 2-position of 1H-pyrrolo[3,2-c]pyridine.

To this end, a method widely used in the case of indole was extrapolated so that 1-methyl-1H-pyrrolo[3,2-c]pyridine was first reacted with tert-butyl lithium at −70° C. and then with N,N-dimethylformamide at the same temperature.

However, these reactions did not lead to the desired compound but to complex mixtures from which only a small portion of the starting product was isolated.

Within the famework of the present invention, attempts were made to provok a selective lithiation in a given position of 1H-pyrrolo[3,2-c]pyridine in accordance with a method described for indole.

Following this procedure, lithiation in the 2-position of the indole was effected from this compound protected in the 1-position, the reaction being carried out in tetrahydrofuran, at 0° C. and by means of lithium diisopropylamide [J. Org. Chem. 46, pp. 2979–2981 (1981)].

When applied to 1H-pyrrolo[3,2-c]pyridine in the same working conditions, this process provides a mixture of numerous products more particularly unreacted starting product, 1H-pyrrolo[3,2-c]pyridine non-substituted in the 1-position and a compound resulting from the addition of lithium diisopropylamide in the pyridine ring.

The impossibility of extrapolating to 1H-pyrrolo[3,2-c]pyridine processes widely known in the indole series was therefore amply demonstrated by these overall results.

As a result of the present invention, 1H-pyrrolo[3,2-c]pyridine derivatives can now be prepared following a process involving protection of 1H-pyrrolo[3,2-c]pyridine in the 1-position, lithiation of the 2-position of the compound so obtained and substitution of the 2-lithio derivative so prepared by means of an appropriate electrophilic reagent.

Thus, an electrophilic group can be fixed, in accordance with the invention, in the 2-position of 1H-pyrrolo[3,2-c]pyridine N-protected in the 1-position following a process which consists in:

(a) Reacting, at room-temperature, 1H-pyrrolo[3,2-c]pyridine in a solvent such as, for example, dichloromethane, by means of an alkali metal hydroxide such as lithium, sodium or potassium hydroxide in the presence of an interphase transfer catalyst such as tetrabutylammonium acid sulphate then, at a temperature between room-temperature and 40° C., with a halide of general formula:

R-Hal in which R represents a labile protecting group and Hal represents a chlorine, bromine or iodine atom, preferably chlorine, to obtain the N-protected 1H-pyrrolo[3,2-c]pyridine derivatives of general formula:

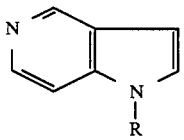

I in which R has the same meaning as above, (b) Reacting in a solvent such as an ether, for example tetrahydrofuran, or an ether/hydrocarbon mixture, for example tetrahydrofuran/pentane, the derivative obtained as described above, with a lithiation agent selected from a lithium amide and an alkyl lithium at a temperature between −80° C. and −20° C. and in the presence of tetramethylethylenediamine to obtain the 2-lithio derivatives of general formula:

<br>

$$\underset{\underset{R}{|}}{\overset{N}{\underset{}{\bigg\langle}}}\text{—Li} \qquad \text{II}$$

in which R has the same meaning as above, (c) Then condensing the metal derivative so obtained in a solvent, such as an ether, for instance tetrahydrofuran, or an ether/hydrocarbon mixture, for instance tetrahydrofuran/pentane, and at a temperature between −80° C. and room-temperature, with a reagent capable of giving rise to an electrophilic group to form 1H-pyrrolo[3,2-c]pyridine derivatives of formula I substituted in the 2-position by an electrophilic group.

By the term "labile protecting group" is meant a group easily removable in alkaline medium more particularly an arylsulphonyl group, such as a benzenesulphonyl or p-toluenesulphonyl group or a group easily removable in acid medium more particularly an alkoxyalkyl group, such as a methoxymethyl group, an aralkyloxyalkyl group, such as a benzyloxymethyl group or a carbalkoxy group, such as a tertbutoxycarbonyl (BOC) group.

Generally speaking, an arylsulfonyl group is preferred, in particular the benzenesulphonyl or p-toluenesulphonyl group or a carbalkoxy group, in particular the BOC group.

Thus, the process of the invention can be used more particularly for preparing the 1H-pyrrolo[3,2-c]pyridine derivatives of general formula:

$$\underset{\underset{R}{|}}{\overset{N}{\underset{}{\bigg\langle}}}\text{—R}_1 \qquad \text{III}$$

R represents a labile protecting group as defined above, $R_1$ represents:
  a lower alkyl group, a phenyl group or a heterocyclic group preferably a furyl or thienyl group
  a group of formula:

$$-\overset{\overset{\text{O}}{\|}}{\text{C}}-\text{R}_2 \qquad \text{(A)}$$

in which $R_2$ represents hydrogen, a lower alkyl group, a group $-OR_3$ in which $R_3$ represents hydrogen or a lower alkyl group or again $R_2$ represents a group $-N(R_4)_2$ in which $R_4$ represents a lower alkyl group,
a group of formula:

$$-\underset{\underset{\text{R}_5}{|}}{\overset{\overset{\text{OH}}{|}}{\text{C}}}-\text{R}_6 \qquad \text{(B)}$$

in which $R_5$ represents hydrogen or a lower alkyl group and $R_6$ represents phenyl or a lower alkyl group,
a silyl group of formula:

$$\text{Si}(R_6)_3 \qquad \text{(C)}$$

in which $R_6$ has the same meaning as above, this process consisting in condensing a metal derivative of formula II in a solvent such as an ether, for example tetrahydrofuran, or an ether/hydrocarbon mixture, for instance a tetrahydrofuran/pentane mixture, and at a temperature between −80° C. and room-temperature, with a reagent capable of giving rise to an electrophilic group selected from the group formed of:
a compound of general formula:

Y-I or Y-SO$_3$CF$_3$ in which Y represents a lower alkyl group, a phenyl group or a heterocyclic group, to obtain the compounds of formula III in which $R_1$ represents a lower alkyl group, a phenyl group or a heterocyclic group
an ester of general formula:

$$\text{H}-\overset{\overset{\text{O}}{\|}}{\text{C}}-\text{OR}_4$$

in which $R_4$ has the same meaning as above, or an anhydride of general formula:

$$(\text{R}_4-\overset{\overset{\text{O}}{\|}}{\text{C}})_2\text{O}$$

in which $R_4$ has the same meaning as above, or carbonic anhydride, or a halide of general formula:

$$\text{Hal}-\overset{\overset{\text{O}}{\|}}{\text{C}}-\text{OR}_4$$

in which $R_4$ and Hal have the same meanings as above, or a halide of general formula:

$$\text{Hal}-\overset{\overset{\text{O}}{\|}}{\text{C}}-\text{N}\underset{\text{R}_4}{\overset{\text{R}_4}{\diagdown}}$$

in which $R_4$ and Hal have the same meanings as above, to obtain the compounds of formula III in which $R_1$ represents a group of formula (A),
an aldehyde or a ketone of general formula:

$$\text{R}_5-\overset{\overset{\text{O}}{\|}}{\text{C}}-\text{R}_6$$

in which $R_5$ and $R_6$ have the same meanings as above, to obtain the compounds of formula III in which $R_1$ represents a group of formula (B),
a silyl halide of general formula:

Hal-Si(R$_6$)$_3$ \qquad (C)

in which Hal and $R_6$ have the same meaning as above, to obtain the compounds of formula III in which $R_1$ represents a group of formula (C).

In the present context, the term of "lower alkyl group" means more particularly the methyl, ethyl, n-propyl or isopropyl group.

The 1H-pyrrolo[3,2-c]pyridine derivatives of formulae I, II and III have been found to be useful as intermediate compounds for chemical synthesis.

Therefore, another object of the invention relates to the compounds of formulae I, II and III as novel industrial products useful as intermediates for chemical synthesis. These compounds may be represented by the general formula:

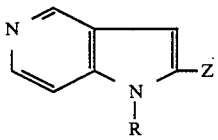

in which R represents a labile protecting group as defined above and Z represents a hydrogen atom, a lithium atom or a group as defined for $R_1$ above.

As indicated above, the preparation of the N-protected derivatives of formula I can be effected starting particularly from a halide. However, it is possible to employ other reagents. For instance, in the case wherein R represents a tert-butoxycarbonyl group, tert-butyl dicarbonate is preferably used.

The alkyl lithium used in the process of the invention can be tert-butyl lithium and the lithium amide is generally lithium 2,2,6,6-tetramethylpiperidide, lithium hexamethyldisilylamide or preferably lithium diisopropylamide.

This last-cited lithium amide also represents the preferred lithiation agent of the invention.

For one equivalent of compounds of formula I, from 1 to 2 equivalents of lithiation agent are used, generally about 1.8 equivalent, and from 2.4 to 3 equivalents of a reagent capable of giving rise to an electrophilic group.

Tetramethylethylenediamine is essentially used for stabilizing the 2-lithio derivatives of formula II by forming ligands.

It has been in fact observed that the absence of tetramethylethylenediamine or again the use of temperatures superior to those employed in the process of the invention provoked a decrease in yield. Generally 1 to 6 equivalents of tetramethylethylenediamine are used for one equivalent of compound of formula I.

Thus, the metalation of the compounds of formula I for the purpose of obtaining the lithium derivatives of formula II can be undertaken in accordance with different procedures in the use of the reagents namely:

Extemporaneous preparation of lithium amide by reacting butyl lithium with the corresponding amine, for instance diisopropylamine, tetramethylpiperdine or hexamethyldisilylamine and addition of this lithium amide to a solution of the compound of formula I and of tetramethylethylenediamine, Extemporaneous preparation of lithium amide by reacting butyl lithium with the corresponding amine in the presence of tetramethylethylenediamine and addition of this solution of lithium amide/tetramethylethylenediamine to a solution of compound of formula I, Addition of tert-butyl lithium to a solution of compound of formula I and of tetramethylethylenediamine, Addition of butyllithium to a mixture of amine, tetramethylethylenediamine (TMEDA) and of compound of formula I, such as, for example, addition of 1.5 equivalent of butyllithium to a mixture of 0.5 equivalent of amine, 1.5 equivalent of TMEDA and 1 equivalent of compound of formula I to form in situ the lithium amide and to obtain the following reaction scheme:

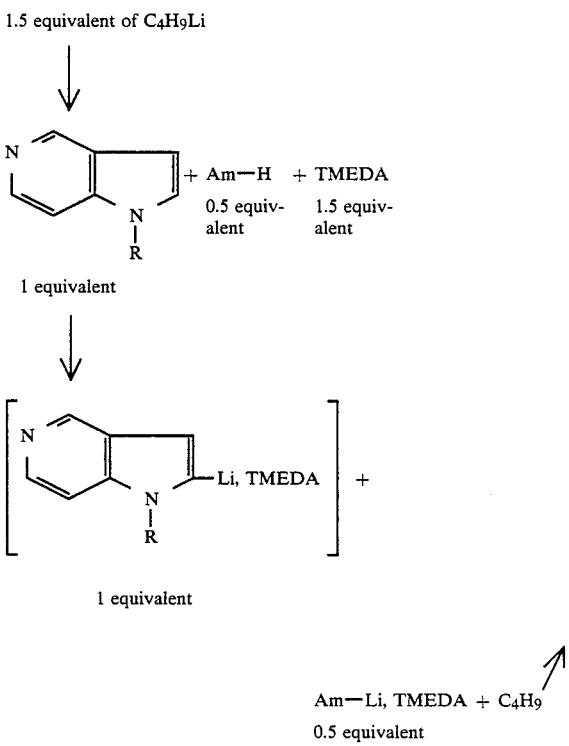

Am = diisopropylamino, tetramethylpiperidino . . .

This last-cited method presents the advantage that only one refrigerated reactor and only one reaction medium must be used. Moreover, only a minimum amount of amine need be employed with respect to the amount of derivative of formula I and displacement of the reaction can be provoked towards the formation of the lithium compound resulting from the evaporation of butane.

Regarding the fixation of the electrophilic group in the 2-position of the lithium compounds of formula II, this operation can also be undertaken in accordance with different procedures such as:

Simultaneous addition to a solution of compound of formula I and of tetramethylethylenediamine, of lithium amide prepared extemporaneously and of reagent capable of giving rise to an electrophilic group, Simultaneous addition to a solution of compound of formula I of lithium amide prepared extemporaneously in the presence of tetramethylethylenediamine and of reagent capable of giving rise to an electrophilic group, Metalation of the compound of formula I as described above to form the lithium derivative of formula II and then condensation with the reagent capable of giving rise to an electrophilic group.

This last-cited method, involving a two-step classical procedure, is sometimes preferable particularly when side-reactions of the lithiation agent with the reagent capable of producing an electrophlic group could arise.

The amount of metal fixed in the 2-position of the compounds of formula I, in particular 1-benzenesulphonyl-1H-pyrrolo[3,2-c]pyridine was easily estimated using trimethylsilyl chloride as reagent capable of producing an electrophilic group, this reagent being inert towards lithium diisopropylamide at −60° C.

The following procedure was used to this end.

A solution of 0.645 g (2.5 mmols) of 1-benzenesulphonyl-1H-pyrrolo[3,2-c]pyridine, 0.377 ml (2.5 mmols) of tetramethylethylenediamine and 0.76 ml (6 mmols) of chlorotrimethylsilane in 5 ml of tetrahydrofuran was cooled to −60° C. After that there were added 4.5 mmols of lithium diisopropylamide obtained by reacting 4.5 mmols of butyllithium and 4.5 mmols of diisopropylamine in 5 ml of tetrahydrofuran at a temperature below 0° C. Thin layer chromatography showed that the reaction was complete after 15 minutes contact at −60° C. The mixture was heated to room-temperature, hydrolysed with 10 ml of 1N-hydrochloric acid and extracted with dichloromethane.

After drying on sodium sulphate and evaporation of the solvent, 0.870 g of a brown gummy product was obtained.

By chromatography on silica, 0.654 g of 1-benzenesulphonyl-2-trimethylsilyl-1H-pyrrolo[3,2-c]pyridine was isolated in the form of a beige-coloured solid which corresponds to a yield of 82.5% (8% of starting product were recuperated).

This method, in which the reagent capable of giving rise to an electrophilic group, is introduced with the metaling agent enables a good estimation to be made of the amount of metal fixed.

The 2-lithio derivative is trapped when formed and the decomposition reactions of this lithium compound or the optional side-reactions are thus reduced to a minimum.

The amount of metal fixed was also estimated by reacting the lithium derivative of formula II with $D_2O$ or $CH_3OD$ (deuteriation) following the scheme:

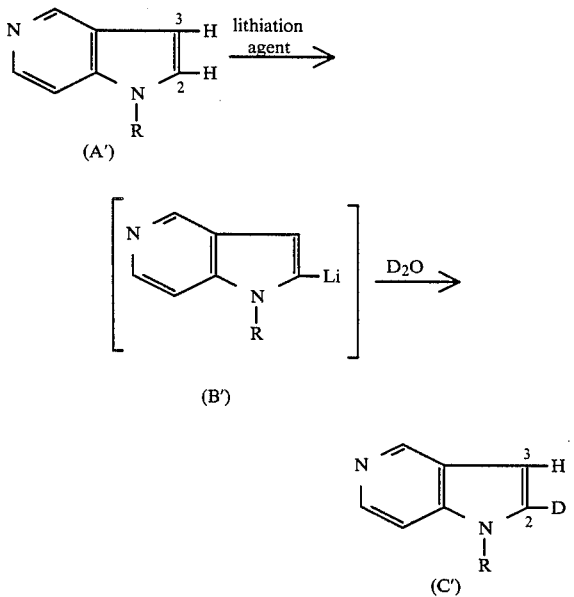

The examination of the nuclear magnetic resonance (N.M.R.) spectrum of $^1H$ of the compounds obtained in crude form showed the disappearance of the two duplets which can be attributed to the $H_2$ and $H_3$ protons of compound (A') giving rise to only one singlet for $H_3$ in compound (C') deuteriated in the 2-position.

The integration of the appropriate signals can provide, with good accuracy, an estimation of the relative amounts of the two kinds of compounds and thus the amount of metal fixed corresponding to $$\frac{\text{compound (C')}}{\text{compound (A') + compound (C')}}$$

For this purpose, the following procedures were used:

(a) Heavy water ($D_2O$) in excess was added to a solution of 1-benzenesulphonyl-2-lithio-1H-pyrrolo[3,2-c]pyridine as described in the following Example 2 from 5 mmols of 1-benzensulphonyl-1H-pyrrolo[3,2-c]pyridine, 7.5 mmols of tetramethylethylenediamine and 7.5 mmols of lithium tetramethylpiperidide previously cooled to −70° C.

After neutralisation to pH=7–8 with 2N-hydrochloric acid, the solvent was evaporated under reduced pressure.

The residue was taken up in dichloromethane and washed with water. After evaporation of the solvent 1.23 g of 1-benzenesulphonyl-2-deuterio-1H-pyrrolo[3,2-c]pyridine were obtained in the form of a beige-brown solid.

Yield: 95%.

Deuteriation level: 85% determined by R.M.N.

$^1H$ N.M.R. spectrum: 6.70 ppm (s, 1H) 85%; 6.75 ppm (d, 1H) 15%; 7.1–8.1 ppm (m, 6H) 100%; 7.60 ppm (d, 1H) 15%; 8.5 ppm (d, 1H) 100%; 8.9 ppm (s, 1H) 100%.

(b) To the solution of 1-tert-butoxycarbonyl-2-lithio-1H-pyrrolo[3,2-c]pyridine obtained in the following Example 12, cooled to −70° C., was added, in one operation, 1.5 ml of heavy water. The temperature increased to −35° C. The mixture was brought to pH=7 by adding 2N-hydrochloric acid and then the solvent was evaporated under vacuum. The residue was taken up in dichloromethane and then washed with water.

In this manner, 0.336 g of 1-tert-butoxycarbonyl-2-deuterio-1H-pyrrolo[3,2-c]pyridine was obtained in the form of a brown oil.

Yield: 61%.

Deuteriation level: 85% determined by R.M.N.

$^1H$ N.M.R. spectrum: 1.65 ppm (s, 9H); 6.6 ppm (s, 1H); 7.95 ppm (d, 1H); 8.45 ppm (d, 1H); 8.75 ppm (s, 1H).

At 7.6 ppm a doublet (15%) remained which corresponded to the starting compound non deuteriated in the 2-position.

(c) Proceeding as described above but with 1-tert-butoxycarbonyl-2-lithio-1H-pyrrolo[3,2-c]pyridine prepared in accordance with the method of Example 11 hereunder, 0.713 g of 1-tert-butoxycarbonyl-2-deuterio-1H-pyrrolo[3,2-c]pyridine was obtained in the form of a brown oil.

Yield: 65%.

Deuteriation level: 90% determined by R.M.N.

Thus, the fixation of an electrophilic group in the 2-position of 1H-pyrrolo[3,2-c]pyridine and more particularly the preparation of the compounds of formula III above can be carried out by condensing the reagent capable of giving rise to the appropriate electrophilic group, such as described above, with the 2-lithium derivative of formula II in the same reaction medium as that in which it forms.

Therefore, another object of the invention concerns a reaction medium intended more particularly to provoke the substitution in the 2-position of a 1H-pyrrolo[3,2- c]pyridine derivative of formula I by an appropriate electrophilic group, reaction medium which is formed of:

A 1H-pyrrolo[3,2-c]pyridine derivative of formula I,
A lithiation agent which is either a lithium amide, for instance lithium 2,2,6,6-tetramethylpiperidide, lithium hexamethyldisilylamide or lithium diisopropylamide, or an alkyl lithium, for example tert-butyllithium,
Tetramethylethylenediamine and
A solvent such as an ether, for example tetrahydrofuran, or an ether/hydrocarbon mixture, for instance tetrahydrofuran/pentane.

The influence of different factors on the yield in compound substituted in the 2-position was studied when the process of the invention was used.

To this end, 1-benzenesulphonyl-2-acetyl-1H-pyrrolo[3,2-c]pyridine was prepared in tetrahydrofuran, at a temperature below $-60°$ C. and varying the amounts of tetramethylethylenediamine (TMEDA) and/or the lithiation agent, the reagent capable of giving rise to an electrophilic group being acetic anhydride:

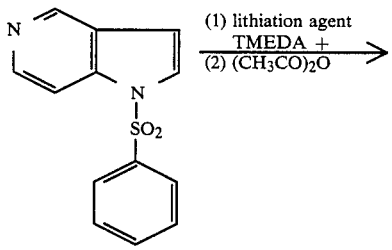

Compound X

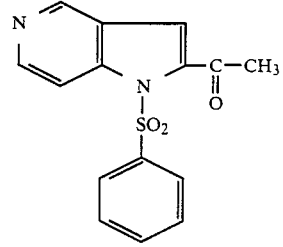

Compound Y (a) Influence of TMEDA

The following results were obtained using lithium diisopropylamide (LiDA) as lithiation agent.

| | Equivalents | | | Yields (%) | |
|---|---|---|---|---|---|
| Compound X | LiDA | TMEDA | $(CH_3CO)_2O$ | Compound X | Compound Y |
| 1 | 1.8 | 6 | 2.4 | 27 | 70 |
| 1 | 1.8 | 1 | 2.4 | 27 | 69 |
| 1 | 1.8 | 0 | 2.4 | 36 | 46 |

(b) Influence of the lithiation agent

| Lithium tetramethylpiperidide (LiTMP) | | | | | |
|---|---|---|---|---|---|
| | Equivalents | | | Yields (%) | |
| Compound X | LiTMP | TMEDA | $(CH_3CO)_2O$ | Compound X | Compound Y |
| 1 | 1.2 | 6 | 2.4 | 20 | 51 |
| 1 | 1.5 | 1.5 | 2.4 | 37 | 55 |
| 1 | 1.8 | 6 | 2.4 | 28 | 65 |
| 1 | 1.2 | 0 | 2.4 | 46 | 17 |

| Lithium hexamethyldisilylamide (LiHMDA) | | | | | |
|---|---|---|---|---|---|
| | Equivalents | | | Yields (%) | |
| Compound X | LiHMDA | TMEDA | $(CH_3CO)_2O$ | Compound X | Compound Y |
| 1 | 1.8 | 6 | 2.4 | 84 | 8 |

| Tert-butyllithium | | | | | |
|---|---|---|---|---|---|
| | Equivalents | | | Yields (%) | |
| Compound X | tBULi | TMEDA | $(CH_3CO)_2O$ | Compound X | Compound Y |
| 1 | 1.2 | 1.2 | 2.4 | 58.5 | 36.5 |
| 1 | 2 | 2 | 2.4 | 31 | 49 |
| 1 | 2 | 0 | 2.4 | 35 | 41 |

The results show the superiority of lithium diisopropylamide as lithiation agent and again prove the valuable influence of tetramethylethylenediamine.

In some cases it is preferable to increase the reactivity of the different compounds involved into the process of the invention so as to improve the yield in 1-R-2-substituted 1H-pyrrolo[3,2-c]pyridine.

This is particularly indicated when the reagent capable of giving rise to the electrophilic group is a phenyl or heterocyclic group.

This increase in reactivity can be obtained for instance by transmetallation from the lithium atom of the compound of formula II to a magnesium or zinc atom using for example magnesium bromide or zinc chloride.

The resulting 2-Mg Br- or 2-Zn Cl- derivative is then reacted with the required reagent capable of giving rise to an electrophilic group for instance phenyl or thienyl iodide in the presence of a catalyst such as palladium/phosphine complexes for instance palladium chloride/1,4-bis(diphenylphosphino)butane complexes.

This reaction can be carried out in an ether such as tetrahydrofuran and at a temperature between −80° C. and room-temperature using 0.01 to 0.03 part of catalyst.

As already stated, the compounds of formulae I, II and III have been found to be particularly useful as intermediates for chemical syntheses.

Owing to their chemical structure, the compounds of formulae I and II, which are preferred compounds, present very valuable possibilities of being transformed on the one hand in view of the lability of the R radical and on the other in view of the wide possibilities of being substituted or modified in the 2-position.

From this viewpoint the compounds of formulae I and II in question are particularly available since they can give rise to anthelmintic derivatives described in J. Med. Chem. 1972, vol. 15, No. 11 pp. 1168–1171.

To this end, the process of the invention is used to fix, as described above, a substituent in the 2-position of a compound of formula I for instance a phenyl or thienyl group, and the resulting compound of formula III is N-deprotected in accordance with classical procedures depending on the nature of the R radical.

Thus, when R represents a labile group removable in alkaline medium the compound of formula III is treated with an alkaline agent for instance an alkali metal hydroxide such as sodium or potassium hydroxide or an alkali metal carbonate such as sodium or potassium carbonate.

Similarly when R represents a labile group removable in acid medium, the compound of formula III is treated with an acid agent for instance a hydrohalic acid such as hydrochloric acid, or yet trifluoroacetic acid.

The following non-limitative Examples illustrate the invention:

EXAMPLE 1

Preparation of 1-benzenesulphonyl-1H-pyrrolo[3,2-c]pyridine

Into 850 ml of dichloromethane were introduced 33.12 g (0.28 mol) of 1H-pyrrolo[3,2-c]pyridine, 28 g (0.70 mol) of crushed sodium hydroxide and 1.09 g (0.0032 mol) of tetrabutylammonium acid sulphate [(n-$C_4H_9)_4N$, $HSO_4$] as interphase transfer catalyst and the the solution so formed was vigorously stirred.

In one hour, 53.7 ml (0.42 mol) of benzenesulphonyl chloride were then added and an increase in temperature was registered from 20° to 40° C. Stirring was maintained for one hour after the addition was terminated. The sodium hydroxide in excess and the sodium chloride formed were then suction-filtered and the filtrate was washed with water to pH=7-8.

After drying on sodium sulphate and partial discolouration on active charcoal the solvent was eliminated under reduced vacuum.

In this manner, 68.4 g of 1-benzenesulphonyl-1H-pyrrolo[3,2-c]pyridine were obtained in the form of a brown solid and with about 90% of purity.

Yield: 83–85% after purification by filtration on silica.

M.P.: 127° C.

I.R. spectrum: $\nu CH$=3140–3120 cm$^{-1}$, $\nu C$=O 1600 cm$^{-1}$, $\nu SO_2$ 1370 cm$^{-1}$.

N.M.R. spectrum 6.8 ppm (d, 1H); 7.5–8 ppm (m, 5H); 7.6 ppm (d, 1H); 8.5 ppm (d, 1H); 8.9 ppm (s, 1H).

| Analysis | C % | H % | N % | S % |
| --- | --- | --- | --- | --- |
| Calculated | 60.45 | 3.90 | 10.85 | 12.41 |
| Found | 60.16 | 3.81 | 10.47 | 12.16 |

EXAMPLE 2

Preparation of 1-benzenesulphonyl-2-lithio-1H-pyrrolo[3,2-c]pyridine

A solution of 1.3 g (5 mmols) of 1-benzenesulphonyl-2-lithio-1H-pyrrolo[3,2-c]pyridine and 0.75 ml (5 mmols) of tetramethylethylenediamine in 10 ml of tetrahydrofuran was cooled to −60° C. Over period of a few minutes there were then added 9 mmols of lithium diisopropylamide (prepared by reacting 9 mmols of butyl lithium and 9 mmols of diisopropylamine in 5 ml of tetrahydrofuran at a temperature below 0° C.) so that the temperature of the medium did not exceed −40° C.

The solution was stirred at −60° C. for 30 minutes.

In this manner, a solution of 1-benzenesulphonyl-2-lithio-1H-pyrrolo[3,2-c]pyridine was obtained which was used as such.

EXAMPLE 3

Preparation of 1-benzenesulphonyl-2-acetyl-1H-pyrrolo[3,2-c]pyridine

To the solution of 1-benzenesulphonyl-2-lithio-1H-pyrrolo[3,2-c]pyridine obtained in Example 2, after cooling to about −70° C., there was added, in one operation, 1.13 ml (12 mmols; 2.4 equivalents) of acetic anhydride and the medium was heated to room-temperature.

The medium was hydrolysed with 50 ml of 1N-hydrochloric acid and then extracted with dichloromethane to provide 1.7 g of a crude product. After chromatography on silica, 0.35 g (about 27%) of starting product and 1.03 g of 1-benzenesulphonyl-2-acetyl-1H-pyrrolo[3,2-c]pyridine were isolated.

Yield: 69%.

M.P.: 205° C.

I.R. spectrum (KBr): $\nu O$=1685 cm$^{-1}$, $\nu SO_2$ 1375 cm$^{-1}$.

N.M.R. spectrum: 2.9 ppm (s, 3H); 7.5–9 ppm (m, 8H); 9.4 ppm (s, 1H).

| Analysis | C % | H % | N % | S % |
| --- | --- | --- | --- | --- |
| Calculated | 59.99 | 4.03 | 9.33 | 10.68 |
| Found | 59.61 | 4.02 | 9.33 | 10.95 |

In the same manner as that described above, 1-benzenesulphonyl-2-trimethylsilyl-1H-pyrrolo[3,2-c]pyridine was prepared from trimethylsilyl chloride and 1-benzenesulphonyl-2-lithio-1H-pyrrolo[3,2-c]pyridine.

M.P.: 125° C.

N.M.R. spectrum: 0.5 ppm (s, 9H); 7 ppm (s, 1H); 7.3–7.9 ppm (m, 6H); 8.4 ppm (d, 1H); 8.9 ppm (s, 1H).

| Analysis | C % | H % | N % | S % |
| --- | --- | --- | --- | --- |
| Calculated | 58.18 | 5.45 | 8.48 | 9.70 |
| Found | 57.98 | 5.48 | 8.54 | 9.52 |

EXAMPLE 4

Preparation of 1-benzenesulphonyl-2-lithio-1H-pyrrolo[3,2-c]pyridine

In 15 ml of tetrahydrofuran were dissolved 1.3 g (5 mmols) of 1-benzenesulphonyl-1H-pyrrolo[3,2-c]pyridine and 4.5 ml (30 mmols) of tetramethylethylenediamine. To this solution, cooled to −70° C., were added in 5 to 10 minutes, 6 mmols of lithium tetramethylpiperidide in 5 ml of tetrahydrofuran (prepared by reacting 6 mmols of butyllithium with 6 mmols of tetramethylpiperidine in tetrahydrofuran at a temperature below 0° C.). Stirring was maintained for 1 hour between −65° C. and −40° C. and then the solution was heated to −20° C.

In this manner, a solution of 1-benzenesulphonyl-2-lithio-1H-pyrrolo[3,2-c]pyridine was obtained which was used as such.

EXAMPLE 5

Preparation of 1-benzenesulphonyl-2-ethoxycarbonyl-1H-pyrrolo[3,2-c]pyridine To the solution of 1-benzenesulphonyl-2-lithio-1H-pyrrolo[3,2-c]pyridine obtained in Example 4, cooled to −70° C., there were added 1.15 ml (12 mmols) of ethyl chloroformiate and the medium was heated to room-temperature. The reaction mixture was neutralized with a 1N-hydrochloric acid solution and then extracted with dichloromethane. After drying of the organic phase on sodium sulphate and evaporation of the solvent, 1.85 g of crude product was obtained.

Chromatography on silica provided 1.23 g of 1-benzenesulphonyl-2-ethoxycarbonyl-1H-pyrrolo[3,2-c]pyridine in the form of a beige-coloured solid.

Yield: 74.5%.
M.P.: 145° C.
I.R. spectrum: $\nu C{=}O$ 1730 cm$^{-1}$. $\nu SO_2$ 1370 cm$^{-1}$.
N.M.R. spectrum: 1.4 ppm (t, 3H); 4.4 ppm (q, 2H); 7.3 ppm (s, 1H); 7.4–8.3 ppm (m, 6H); 8.6 ppm (d, 1H); 9 ppm (s, 1H).

| Analysis | | | | |
|---|---|---|---|---|
| | C % | H % | N % | S % |
| Calculated | 58.17 | 4.27 | 8.48 | 9.71 |
| Found | 57.91 | 4.25 | 8.21 | 9.56 |

Using the same method as that described above, 1-benzenesulphonyl-2-methoxycarbonyl-1H-pyrrolo[3,2-c]pyridine was prepared from methyl chloroformiate and 1-benzenesulphonyl-2-lithio-1H-pyrrolo[3,2-c]pyridine.

M.P.: 166° C.
I.R. spectrum (KBr): $\nu C{=}O$ 1720 cm$^{-1}$, $\nu SO_2$ 1377 cm$^{-1}$.
N.M.R. spectrum (CDCl$_3$/tetramethylsilane/trifluoroacetic acid) 3.9 ppm (s, 3H); 7.3–9.4 ppm (m, 9H).

EXAMPLE 6

Preparation of 1-benzenesulphonyl-2-lithio-1H-pyrrolo[3,2-c]pyridine

In 15 ml of tetrahydrofuran were dissolved 1.3 g (5 mmols) of 1-benzenesulphonyl-1H-pyrrolo[3,2-c]pyridine and 9 mmols of tetramethylethylenediamine. To this solution, cooled at a temperature below −60° C., were added, in 5 to 10 minutes, 9 mmols of lithium diisopropylamide prepared by reaction of 9 mmols of butyllithium and 9 mmols of diisopropylamine in tetrahydrofuran.

Stirring was maintained for 15 to 30 minutes at −60° C. and a control was made by thin layer chromatography to verify whether the metalation was complete by reaction of an aliquot fraction of the reaction medium with trimethylsilane in excess.

In this manner, a solution of 1-benzenesulphonyl-2-lithio-1H-pyrrolo[3,2-c]pyridine was obtained which was used as such.

EXAMPLE 7

Preparation of 1-benzenesulphonyl-1H-pyrrolo[3,2-c]pyridine derivatives substituted in the 2-position by an electrophilic group To the solution of 1-benzenesulphonyl-2-lithio-1H-pyrrolo[3,2-c]pyridine obtained in Example 6, there were added 12 to 15 mmols of reagent capable of giving rise to an electrophilic group and the evolution of the reaction was followd by thin layer chromatography. The reaction medium was neutralized by 1N-hydrochloric acid and extracted with dichloromethane. After drying and evaporating the organic phases, the residue was purified by filtration on silica.

In this manner, the following compounds were obtained:

(a) 1-Benzenesulphonyl-2-formyl-1H-pyrrolo[3,2-c]pyridine

Reagent giving rise to the electrophilic group: ethyl formiate.
Yield: 52%.
M.P.: 164° C.
I.R. spectrum (KBr): $\nu C{=}O$ 1686 cm$^{-1}$, $\nu C{=}H$ 2930 cm$^{-1}$, $\nu SO_2$ 1378 cm$^{-1}$.
N.M.R. spectrum (CDCl$_3$/TMS): 7.2–9.1 ppm (m, 9H); 10.45 ppm (s, 1H).

(b) 1-Benzenesulphonyl-2-hydroxycarbonyl-1H-pyrrolo[3,2-c]pyridine

Reagent giving rise to the electrophilic group: solid carbonic anhydride
Yield: 80%
I.R. spectrum: $\nu C{=}O$ 1600 cm$^{-1}$, $\nu SO_2$ 1384 cm$^{-1}$.

(c) 1-Benzenesulphonyl-2-(1-hydroxy-ethyl)-1H-pyrrolo[3,2-c]pyridine

Reagent giving rise to the electrophilic group: acetaldehyde
Yield: 48%.
M.P.: 185° C.
N.M.R. spectrum (CDCl$_3$/DMSOD$_6$/$\epsilon$TFA/TMS): 1.55 ppm (d, J=6.5 Hz, 3H); 3.45 ppm (q, J=6.5 Hz, 1H); 7.2 ppm (s, 1H); 7.5–9.4 ppm (m, 8H).

(d) 1-Benzenesulphonyl-2-(1-hydroxy-1-phenyl-ethyl)-1H-pyrrolo[3,2-c]pyridine

Reagent giving rise to the electrophilic group: acetophenone
Yield: 69%.
M.P.: 150° C.
N.M.R. spectrum (CDCl$_3$/TMS): 1.95 ppm (s, 3H); 7.1–7.6 ppm (m, 5H); 7.95 ppm (d, J=6 Hz, 1H); 8.5 ppm (d, J=6 Hz, 1H); 8.9 ppm (s, 1H).

(e) 1-Benzenesulphonyl-2-diethylaminocarbonyl-1H-pyrrolo[3,2-c]pyridine

Reagent giving rise to the electrophilic group: diethylcarbamyl chloride
Yield: 20%.

I.R. (film): $\nu C=O$ 1730 cm$^{-1}$, $\nu SO_2$ 1377 cm$^{-1}$.

N.M.R. (CDCl$_3$/TMS): 1.25 ppm (m, 6H); 3.4 ppm (m, 4H); 7.2–9 ppm (m, 9H).

(f) 1-Benzenesulphonyl-2-ethyl-1H-pyrrolo[3,2-c]pyridine

Reagent giving rise to the electrophilic group: ethyl iodide

Yield: 21%.

M.P.: 121° C.

N.M.R. (CDCl$_3$/TMS): 1.4 ppm (t, J=7 Hz, 3H); 3 ppm (q, J=7 Hz, 2H); 6.45 ppm (s, 1H); 7.2–7.9 ppm (m, 5H); 8.05 ppm (d, J=6 Hz, 1H); 8.4 ppm (d, J=6 Hz, 1H); 8.75 ppm (s, 1H).

EXAMPLE 8

Preparation of 1-benzenesulphonyl-2-lithio-1H-pyrrolo[3,2-c]pyridine

A solution of 0.645 g (2.5 mmols) of 1-benzenesulphonyl-1H-pyrrolo[3,2-c]pyridine and 0.755 ml (5 mmols) of tetramethylethylenediamine in 5 ml of tetrahydrofuran was cooled to −70° C. and 5 mmols of tert-butyl lithium in pentane were added, care being taken that the temperature did not exceed −60° C. The reaction medium was then stirred to obtain a solution of 1-benzenesulphonyl-2-lithio-1H-pyrrolo[3,2-c]pyridine which was used as such.

EXAMPLE 9

Preparation of 1-benzenesulphonyl-2-acetyl-1H-pyrrolo[3,2-c]pyridine

The solution of 1-benzenesulphonyl-2-lithio-1H-pyrrolo[3,2-c]pyridine obtained in Example 8 was brought to −70° C. and 0.5 g (6 mmols) of acetic anhydride was added in one operation.

After heating to room-temperature and isolation as in Example 3, a chromatography provided 0.365 g of 1-benzenesulphonyl-2-acetyl-1H-pyrrolo[3,2-c]pyridine.

Yield: 49%.

EXAMPLE 10

Preparation of 1-tert-butoxycarbonyl-1H-pyrrolo[3,2-c]pyridine

Following the same method as that described in Example 1 but starting from 22.6 g (0.2 mol) of 1H-pyrrolo[3,2-c]pyridine and 55 ml (0.24 mol) of tert-butyl dicarbonate, there were obtained 42.5 g of a brown oil which crystallized in the refrigerator.

By chromatographic purification of an analytical sample, 1-tert-butoxycarbonyl-1H-pyrrolo[3,2-c]pyridine was obtained in the form of a cream-coloured powder.

M.P.: 65° C.

I.R. spectrum:
$\nu C=O$ 1735 cm$^{-1}$.

N.M.R. spectrum: 1.65 ppm (s, 9H); 6.6 ppm (d, 1H); 7.65 ppm (d, 1H); 7.95 ppm (d, 1H); 8.45 ppm (d, 1H); 8.75 ppm (s, 1H).

| Analysis | C % | H % | N % |
|---|---|---|---|
| Calculated | 66.04 | 6.47 | 12.83 |
| Found | 66.20 | 6.51 | 13.10 |

EXAMPLE 11

Preparation of 1-tert-butoxycarbonyl-2-lithio-1H-pyrrolo[3,2-c]pyridine

A solution of 1.092 g (5 mmols) of 1-tert-butoxycarbonyl-1H-pyrrolo[3,2-c]pyridine, 1.14 ml (7.5 mmols) of tetramethylethylenediamine and 0.42 ml (2.5 mmols) of tetramethylpiperidine in 7.6 ml of tetrahydrofuran was cooled to −70° C. In 15 minutes, 7.5 mmols of butyllithium was then added while the temperature was maintained below −60° C. and the red-brown solution obtained was stirred for 30 minutes at this temperature.

In this manner, a solution of 1-tert-butoxycarbonyl-2-lithio-1H-pyrrolo[3,2-c]pyridine was obtained which was used as such.

EXAMPLE 12

Preparation of 1-tert-butoxycarbonyl-2-lithio-1H-pyrrolo[3,2-c]pyridine

A solution of 0.549 g (2.5 mmols) of 1-tert-butoxycarbonyl-1H-pyrrolo[3,2-c]pyridine and of 0.76 ml (5 mmols) of tetramethylethylenediamine in 2.5 ml of tetrahydrofuran was cooled to −70° C.

Over a period of a few minutes, 5 mmols of lithium tetramethylpiperidide (prepared by reaction of 5 mmols of butyllithium and 5 mmols of tetramethylpiperidine in 2.5 ml of tetrahydrofuran at a temperature below −20° C.) were then added so that the temperature of the medium did not exceed −60° C. The red-brown solution so obtained was stirred for 30 minutes at a temperature inferior or equal to −60° C.

In this manner, a solution of 1-tert-butoxycarbonyl-2-lithio-1H-pyrrolo[3,2-c]pyridine was obtained which was used as such.

EXAMPLE 13

Preparation of 1-tert-butoxycarbonyl-2-trimethylsilyl-1H-pyrrolo[3,2-c]pyridine

To the solution of 1-tert-butoxycarbonyl-2-lithio-1H-pyrrolo[3,2-c]pyridine obtained in Example 12, cooled to −70° C., there was added 0.48 ml (3.8 mmols) of trimethylsilylchloride. The temperature increased to −50° C. The mixture was heated to room-temperature and the pH was brought to 7 by adding 2N-hydrochloric acid. The solvent was evaporated off under reduced pressure and the residue was taken up in dichloromethane. After washing with water and drying on magnesium sulphate, the solvent was evaporated off to provide 0.65 g of a off-white solid. After chromatographic purification on silica, 0.561 g of 1-tert-butoxycarbonyl-2-trimethylsilyl-1H-pyrrolo[3,2-c]pyridine was obtained in the form of a white solid.

Yield: 78%.

M.P.: 112° C.

I.R. spectrum: $\nu C=O$ 1735 cm$^{-1}$.

N.M.R. spectrum 0.04 ppm (s, 9H); 1.65 ppm (s, 9H); 6.85 ppm (s, 1H); 7.95 ppm (d, 1H); 8.45 ppm (d, 1H); 8.7 ppm (s, 1H).

Using the same method as above, 1-tert-butoxycarbonyl-2-(1-hydroxy-1-phenyl-methyl)-1H-pyrrolo[3,2-c]pyridine was obtained from 1-tert-butoxycarbonyl-2-lithio-1H-pyrrolo[3,2-c]pyridine and benzaldehyde.

Yield: 76%.

I.R. spectrum: $\nu C{=}O$ 1735 cm$^{-1}$.

N.M.R. spectrum: 1.4 ppm (s, 9H); 6.60 ppm (s, 1H); 7.1–7.9 ppm (m, 7H); 8.4 ppm (d, 1H); 9.1 ppm (s, 1H).

EXAMPLE 14

Preparation of 2-phenyl-1H-pyrrolo[3,2-c]pyridine from compounds of the invention In 15 ml of tetrahydrofuran were dissolved 5 mmols of 1-benzenesulphonyl-1H-pyrrolo[3,2-c]pyridine and 9 mmols of tetramethylethylenediamine. The solution was cooled at a temperature below −60° C. and 9 mmols of lithium diisopropylamide, prepared by reaction of 9 mmols of butyllithium and 9 mmols of diisopropylamine in tetrahydrofuran, were added in 5 to 10 minutes. minutes.

Stirring was maintained for 15 to 30 minutes at −60° C. and the evolution of the reaction metallation was followed by thin layer chromatography.

The solution of 1-benzenesulphonyl-2-lithio-1H-pyrrolo[3,2-c]pyridine so obtained was then added to a mixture of 6.3 mmols of magnesium bromide in 10 ml of tetrahydrofuran at room-temperature. The mixture was stirred at room-temperature for 1 hour. While stirring the solution of 1-benzenesulphonyl-2-bromomagnesio-1H-pyrrolo[3,2-c]so formed was added, at room-temperature and under argon atmosphere, to a mixture of 2.6 mmols of iodobenzene and 0.07 mmols of palladium chloride/1,4-bis (diphenylphosphino)butane. The mixture was then stirred for 20 hours.

The reaction medium was neutralized by 1N-hydrochloric acid and extracted with dichloromethane. After drying and evaporating the organic phase, the residue was taken up in 40 ml of methanol and a solution of 20 mmols of potassium carbonate in 20 ml of water added. The mixture was heated to 65° C. for one hour and then cooled. The solvent was evaporated under reduced pressure and the aqueous phase was extracted twice 30 ml of dichloromethane. The organic phase was dried on sodium sulphate and the solvent was eliminated under reduced pressure. The crude product so provided was then purified by chromatography.

In this manner, 2-phenyl-1H-pyrrolo[3,2-c]pyridine was obtained in a yield of 68.3%.

We claim:

1. A 1H-pyrrolo[3,2-c]pyridine derivative of the formula:

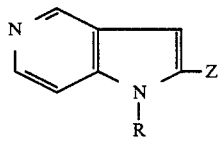

in which R represents a labile protecting group selected from the group consisting of alkoxyalkyl, aralkyloxyalkyl, arylsulphonyl and carbalkoxy groups, and Z represents a hydrogen or lithium atom.

2. A 1H-pyrrolo[3,2-c]pyridine derivative according to claim 1 wherein the labile protecting group is a benzenesulphonyl or tert-butoxycarbonyl group.

3. 1-Benzenesulphonyl-1H-pyrrolo[3,2-c]pyridine.

4. 1-Benzenesulphonyl-2-lithio-1H-pyrrolo[3,2-c]pyridine.

5. The compound of claim 1 which is 1-Tert-butoxycarbonyl-1H-pyrrolo[3,2-c]pyridine.

6. The compound of claim 1 which is 1-Tert-butoxycarbonyl-2-lithio-1H-pyrrolo[3,2-c]pyridine.

* * * * *